United States Patent
Hudson et al.

(10) Patent No.: US 11,893,223 B2
(45) Date of Patent: Feb. 6, 2024

(54) PRESSURE CONTROL IN PAP SYSTEMS

(71) Applicant: ResMed Pty Ltd, Bella Vista (AU)

(72) Inventors: Robert Hudson, Bella Vista (AU); Rowan Furlong, Bella Vista (AU)

(73) Assignee: RESMED PTY LTD, Bella Vista (AU)

( * ) Notice: Subject to any disclaimer, the term of this patent is extended or adjusted under 35 U.S.C. 154(b) by 0 days.

(21) Appl. No.: 18/056,589

(22) Filed: Nov. 17, 2022

(65) Prior Publication Data

US 2023/0077509 A1   Mar. 16, 2023

Related U.S. Application Data

(63) Continuation of application No. 16/878,852, filed on May 20, 2020, now Pat. No. 11,537,282.

(60) Provisional application No. 62/850,538, filed on May 20, 2019.

(51) Int. Cl.
| | |
|---|---|
| *G06F 3/04847* | (2022.01) |
| *A61M 16/00* | (2006.01) |
| *F04B 49/08* | (2006.01) |
| *G06F 3/0488* | (2022.01) |

(52) U.S. Cl.
CPC ..... *G06F 3/04847* (2013.01); *A61M 16/0066* (2013.01); *A61M 16/022* (2017.08); *F04B 49/08* (2013.01); *G06F 3/0488* (2013.01); *A61M 2205/3344* (2013.01); *A61M 2205/505* (2013.01)

(58) Field of Classification Search
CPC .............. G06F 3/04847; G06F 3/0488; G06F 3/04886; A61M 16/0066; A61M 16/022; A61M 2205/3344; A61M 2205/505; F04B 49/08; F04B 49/065
See application file for complete search history.

(56) References Cited

U.S. PATENT DOCUMENTS

| | | | |
|---|---|---|---|
| 4,867,152 A * | 9/1989 | Kou | A61M 16/00 600/536 |
| 5,931,160 A | 8/1999 | Gilmore et al. | |
| 6,369,838 B1 | 4/2002 | Wallace | |
| 6,425,861 B1 | 7/2002 | Haberland et al. | |
| 6,543,449 B1 | 4/2003 | Woodring et al. | |
| 7,040,321 B2 * | 5/2006 | Gobel | A61M 16/044 128/207.14 |

(Continued)

FOREIGN PATENT DOCUMENTS

| | | | | |
|---|---|---|---|---|
| CN | 105664314 A | * | 6/2016 | |
| CN | 109032468 B | * | 11/2020 | ......... G06F 3/04847 |

(Continued)

OTHER PUBLICATIONS

How to disable dropdown options less than some value using jquery, retrieved from—https://stackoverflow.com/questions/30601314/how-to-disable-dropdown-options-less-than-some-value-using-jquery, Jun. 2, 2015, 3 pages (Year: 2015).*

Slider filter with drill capability, Apr. 29, 2014, 6 pages (Year: 2014).*

(Continued)

*Primary Examiner* — Yongjia Pan

(74) *Attorney, Agent, or Firm* — Nixon & Vanderhye P.C.

(57) ABSTRACT

A respiratory therapy device, which may include a flow generator, is provided. The RPT device includes a touch screen display that displays user interface screens to a user and accepts input from users to control parameters and functionality of the RPT device (e.g., a flow generator).

20 Claims, 6 Drawing Sheets

(56) References Cited

U.S. PATENT DOCUMENTS

| | | | |
|---|---|---|---|
| 7,270,126 B2 | 9/2007 | Wallace | |
| 7,866,944 B2 | 1/2011 | Kenyon et al. | |
| 7,958,892 B2 | 6/2011 | Kwok et al. | |
| 8,015,972 B2 | 9/2011 | Pirzada | |
| 8,302,602 B2 | 11/2012 | Andrieux et al. | |
| 8,393,323 B2 | 3/2013 | Andrieux et al. | |
| 8,539,952 B2 | 9/2013 | Carbone et al. | |
| 8,636,479 B2 | 1/2014 | Kenyon et al. | |
| 8,638,014 B2 | 1/2014 | Sears et al. | |
| 8,640,700 B2 | 2/2014 | Baker | |
| 8,746,247 B2 | 6/2014 | Mechlenburg | |
| 8,924,878 B2 * | 12/2014 | Palmer | G06F 3/0488 715/764 |
| 8,990,732 B2 * | 3/2015 | Farrenkopf | G06F 3/04855 715/833 |
| 9,155,853 B2 | 10/2015 | Knor | |
| 9,375,543 B2 | 6/2016 | Librett et al. | |
| 9,392,963 B2 | 7/2016 | Krans et al. | |
| 9,539,401 B2 | 1/2017 | Tatkov | |
| 9,750,907 B2 | 9/2017 | Librett et al. | |
| 9,772,759 B2 * | 9/2017 | Hogan | G06F 3/04847 |
| 9,814,850 B2 | 11/2017 | Paul | |
| 9,872,965 B2 | 1/2018 | Baloa Welzien et al. | |
| 9,901,692 B2 | 2/2018 | Mechlenburg et al. | |
| 9,981,099 B2 | 5/2018 | Feldhahn et al. | |
| 9,993,608 B2 | 6/2018 | Cheung et al. | |
| 10,105,506 B2 | 10/2018 | Bassin et al. | |
| 10,296,181 B2 * | 5/2019 | Lahtivuori | G06F 3/0482 |
| 10,496,265 B2 * | 12/2019 | Bhargava | G06F 3/04847 |
| 10,845,973 B2 * | 11/2020 | Lahtivuori | G06F 3/04842 |
| 11,287,965 B2 * | 3/2022 | Lindström | G16H 20/40 |
| 11,517,689 B2 * | 12/2022 | Bao | G16H 40/67 |
| 2002/0026941 A1 * | 3/2002 | Biondi | A61M 16/026 128/204.21 |
| 2003/0062045 A1 | 4/2003 | Woodring | |
| 2005/0115561 A1 | 6/2005 | Stahmann | |
| 2008/0072896 A1 | 3/2008 | Setzer | |
| 2009/0107498 A1 | 4/2009 | Plattner | |
| 2009/0149927 A1 * | 6/2009 | Kneuer | A61G 11/008 345/173 |
| 2009/0241956 A1 * | 10/2009 | Baker, Jr. | A61M 16/12 128/204.23 |
| 2010/0011307 A1 | 1/2010 | Desfossez et al. | |
| 2011/0041849 A1 * | 2/2011 | Chen | A61M 16/026 128/204.23 |
| 2011/0138308 A1 * | 6/2011 | Palmer | G16H 40/63 715/763 |
| 2011/0164002 A1 | 7/2011 | Hill | |
| 2011/0310004 A1 * | 12/2011 | Trasler | G06F 3/04855 345/156 |
| 2012/0096381 A1 | 4/2012 | Milne | |
| 2013/0055134 A1 * | 2/2013 | Knor | A61M 16/021 128/204.21 |
| 2014/0014110 A1 | 1/2014 | Adams | |
| 2015/0100916 A1 * | 4/2015 | Hanumara | G06F 3/0485 715/785 |
| 2015/0133809 A1 | 5/2015 | Paul | |
| 2015/0144130 A1 | 5/2015 | O'Donnell et al. | |
| 2015/0277733 A1 | 10/2015 | Schwaibold | |
| 2016/0202890 A1 * | 7/2016 | Feldhahn | A61M 16/024 715/771 |
| 2016/0213869 A1 | 7/2016 | Feldhahn et al. | |
| 2016/0256642 A1 | 9/2016 | Soysa et al. | |
| 2017/0014585 A1 | 1/2017 | Gerred et al. | |
| 2017/0224234 A1 | 8/2017 | Ahlmen et al. | |
| 2017/0361133 A1 | 12/2017 | Yu et al. | |
| 2018/0085544 A1 | 3/2018 | Holyoake et al. | |
| 2018/0103898 A1 | 4/2018 | Robinson | |
| 2018/0185606 A1 | 7/2018 | Van Schalkwyk et al. | |
| 2018/0349005 A1 * | 12/2018 | Bhargava | G06F 3/04847 |
| 2019/0026261 A1 | 1/2019 | Kludy | |
| 2019/0076617 A1 | 3/2019 | Smith et al. | |
| 2019/0150831 A1 | 5/2019 | Payton et al. | |
| 2019/0167929 A1 * | 6/2019 | Cox | A61M 16/0066 |
| 2019/0175857 A1 | 6/2019 | Whiting et al. | |
| 2021/0181932 A1 * | 6/2021 | Han | G06F 3/04847 |

FOREIGN PATENT DOCUMENTS

| | | | | |
|---|---|---|---|---|
| CN | 115061618 A | * | 9/2022 | |
| DE | 10 2012 10 7078 | | 2/2013 | |
| FR | 3038748 B1 | * | 6/2019 | A61B 5/091 |
| GB | 2465028 A | * | 5/2010 | G06F 3/04847 |
| WO | WO1997020592 A1 | * | 6/1997 | A61M 16/00 |
| WO | 2013/020167 | | 2/2013 | |
| WO | 2015/027980 | | 3/2015 | |

OTHER PUBLICATIONS

Date Range Selection, retrieved from—< https://experience.sap.com/fiori-design-web/v1-26/date-range-selection/>, 11 pages, (Dec. 19, 2016).

How can I validate that the max field is greater than the min field, retrieved from—<https://stackoverflow.com/questions/14347177/>, how-can-i-validate-that-the-max-field-is-greater-than-the-min-field, 4 pages, (Jan. 16, 2013).

Change button color if input is valid, retrieved from—<https://stackoverflow.com/questions/49451793/> change-button-color-if-input-is-valid, 2 pages, (Mar. 23, 2018).

How to disable dropdown options less than some value using jquery, retrieved from—https://stackoverflow.com/questions/30601314> how-to-disable-dropdown-options-less-than-some-value-using-jquery, 3 pages, (Jun. 2, 2015).

JOptionPane—check user input and prevent from closing until conditions are met, retrieved from—<https://stackoverflow.com/>questions/13055107/joptionpane-check-user-input-and-prevent-from-closing-until-conditions-are-met, 10 pages, (Oct. 24, 2012).

* cited by examiner

PRESSURE CONTROL IN PAP SYSTEMS

This application is a continuation of U.S. patent application Ser. No. 16/878,852, filed May 20, 2020, now allowed; which claims priority to U.S. Provisional Application No. 62/850,538, filed May 20, 2019, the entire contents of which are hereby incorporated by reference.

TECHNICAL OVERVIEW

The technology described herein relates techniques for controlling positive airway pressure (PAP) devices (e.g. CPAP, APAP, BPAP) that control pressure levels. More particularly, the technology described herein relates to touch screen techniques for controlling pressure that is provided by a flow generator or the like.

INTRODUCTION

Medical devices play an important role today's society. Such devices can provide important benefits to those using them. However, the interfaces or control systems for controlling such devices can leave users frustrated. Accordingly, new and improved techniques, systems, and processes that facilitate control of such medical devices are continually sought after.

SUMMARY

A respiratory therapy device, which may be a flow generator, is provided. The RPT device includes a touch screen display that displays user interface screens to a user and accepts input from users to control parameters and functionality of the RPT device (e.g., a flow generator). In certain example embodiments, the touch screen display may be provided separately from the RPT device and used to control functionality of the RPT device via wireless or wired communication. For example, the touch screen functionality may be provided in connection with a graphical user interface that is presented via a mobile device (e.g., a mobile phone, tablet, or the like) that is in communication with the RPT device.

This Summary is provided to introduce a selection of concepts that are further described below in the Detailed Description. This Summary is intended neither to identify key features or essential features of the claimed subject matter, nor to be used to limit the scope of the claimed subject matter; rather, this Summary is intended to provide an overview of the subject matter described in this document. Accordingly, it will be appreciated that the above-described features are merely examples, and that other features, aspects, and advantages of the subject matter described herein will become apparent from the following Detailed Description, Figures, and Claims.

BRIEF DESCRIPTION OF THE DRAWINGS

These and other features and advantages will be better and more completely understood by referring to the following detailed description of example non-limiting illustrative embodiments in conjunction with the drawings of which.

DETAILED DESCRIPTION

In the following description, for purposes of explanation and non-limitation, specific details are set forth, such as particular nodes, functional entities, techniques, protocols, etc. in order to provide an understanding of the described technology. It will be apparent to one skilled in the art that other embodiments may be practiced apart from the specific details described below. In other instances, detailed descriptions of well-known methods, devices, techniques, etc. are omitted so as not to obscure the description with unnecessary detail.

Sections are used in this Detailed Description solely in order to orient the reader as to the general subject matter of each section; as will be seen below, the description of many features spans multiple sections, and headings should not be read as affecting the meaning of the description included in any section.

In many places in this document, software modules and actions performed by software modules are described. This is done for ease of description; it should be understood that, whenever it is described in this document that a software module performs any action, the action is in actuality performed by underlying hardware elements (such as a processor and a memory device) according to the instructions that comprise the software module. Further details regarding this are provided below in, among other places, the description of FIG. 5.

Figure 1A:
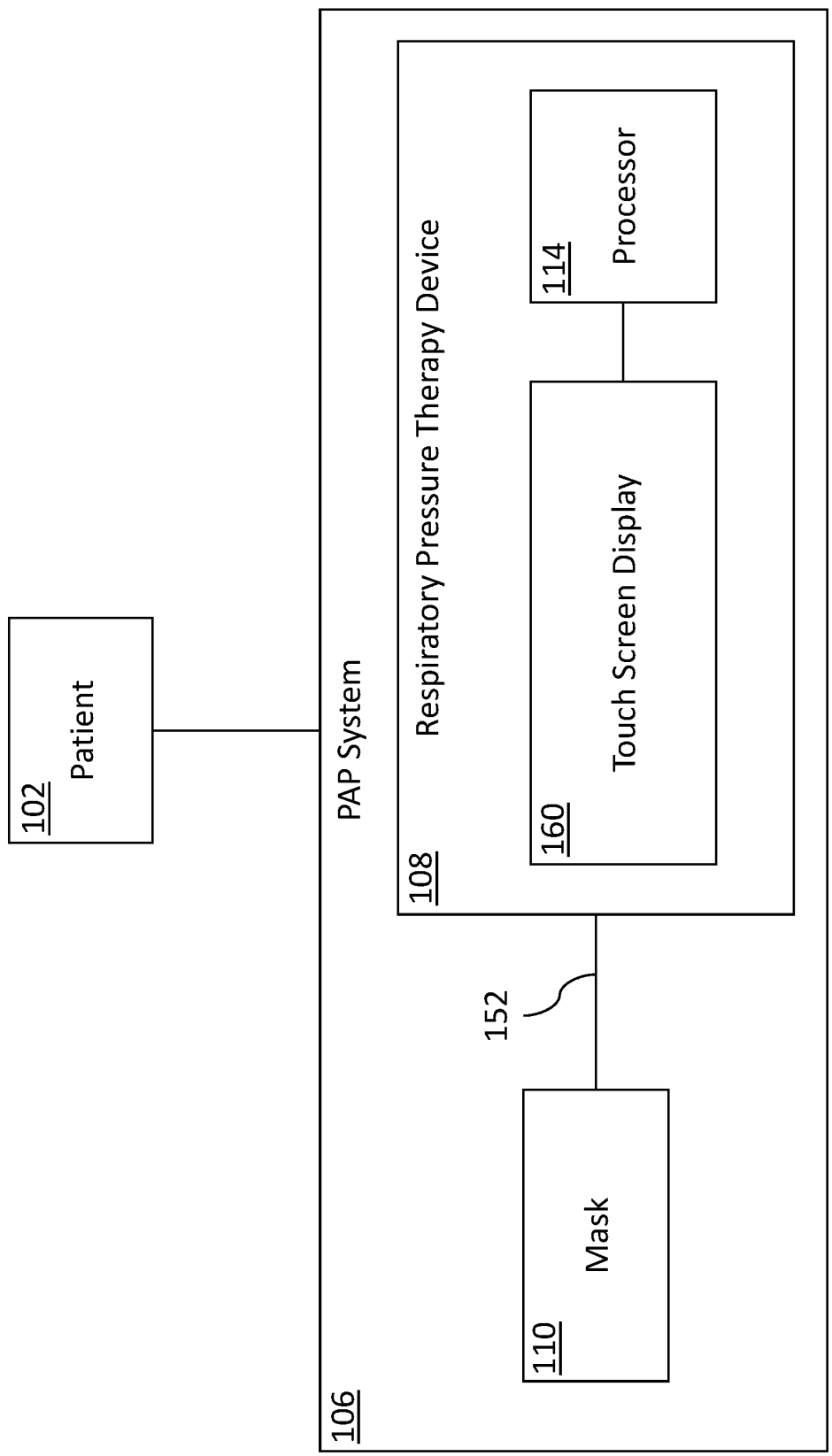
FIG. 1A is a system diagram that includes a PAP system according to certain examples.
Figure 1B:
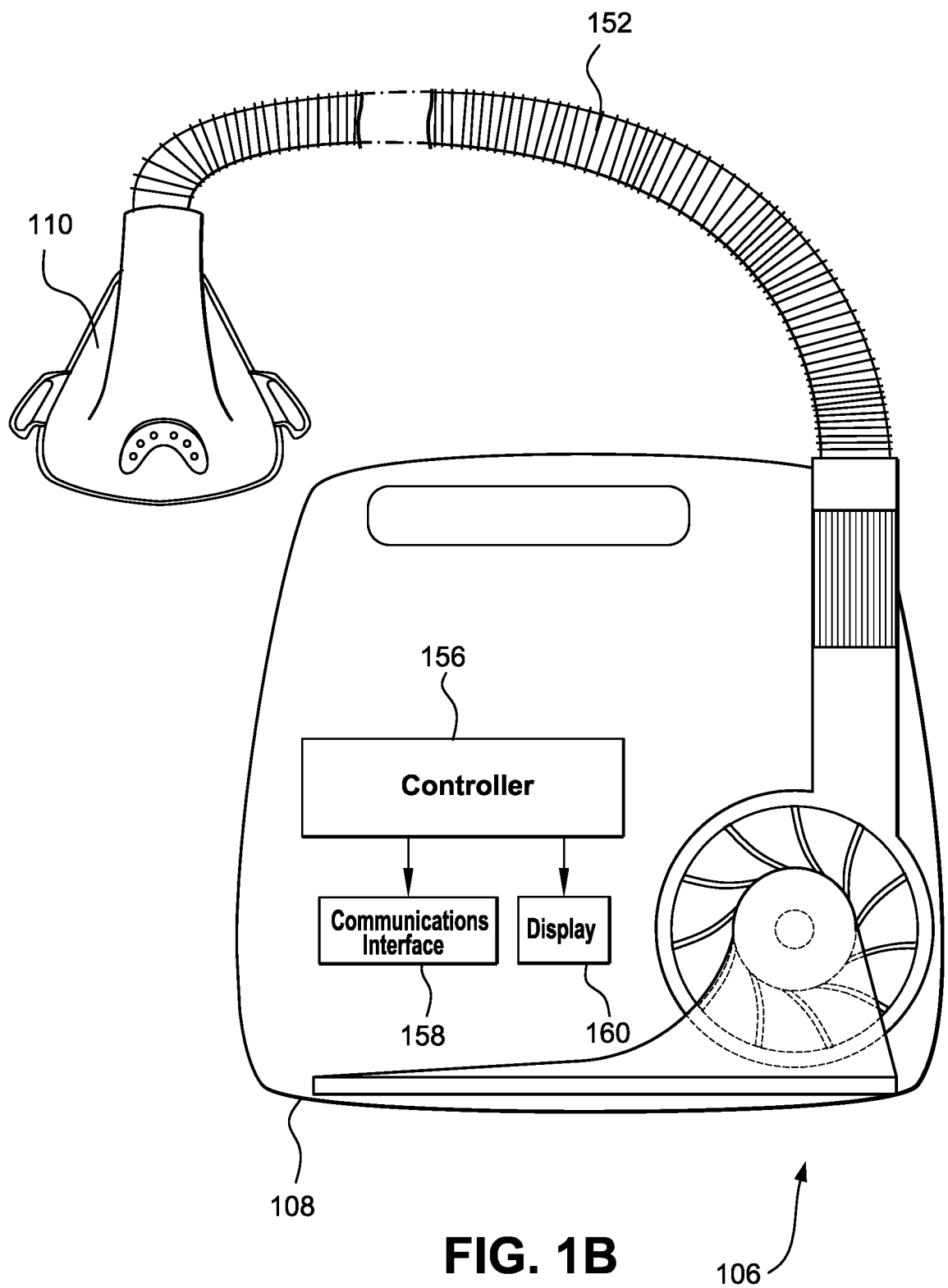
FIG. 1B shows an example PAP system according to certain examples.

FIG. 1A is a system diagram that includes a PAP system 106 usable by a patient 102. FIG. 1B shows an example of the PAP system 106 of FIG. 1A.

PAP system 106 includes PAP components that may be, for example, a patient interface or mask 110, a humidifier (not shown), and air conduit 152, and a Respiratory Pressure Therapy Device or RPT device 108. The PAP system 106 may be a CPAP, APAP, or a BPAP system. An example of an RPT device may be a flow generator. The RPT device 108 includes a touch screen display 160 and a processor 114 (e.g., contained in the housing of the RPT device 108). The touch screen display 160 may be a resistive or capacitive type display. Other types of touch screens are also possible. The processor 114 may, in certain examples, be a computing system, such as computing system 500 described in connection with FIG. 5 or a component of computing system 500, such as processing system 502.

The patient 102 (or another user) interacts with the touch screen display 160 to control the operation of the RPT device. For example, pressure levels or pressure ranges that are used to control operation of the RPT device 108 may be set by a user. Each or any of the user interface screens shown in FIG. 3-5 may be generated by the processor 114 and/or displayed on display 160. Input may be provided in connection with the displayed screens by a user touching on the screen in correspondence with a location of an icon, button, or the like.

Figure 3:
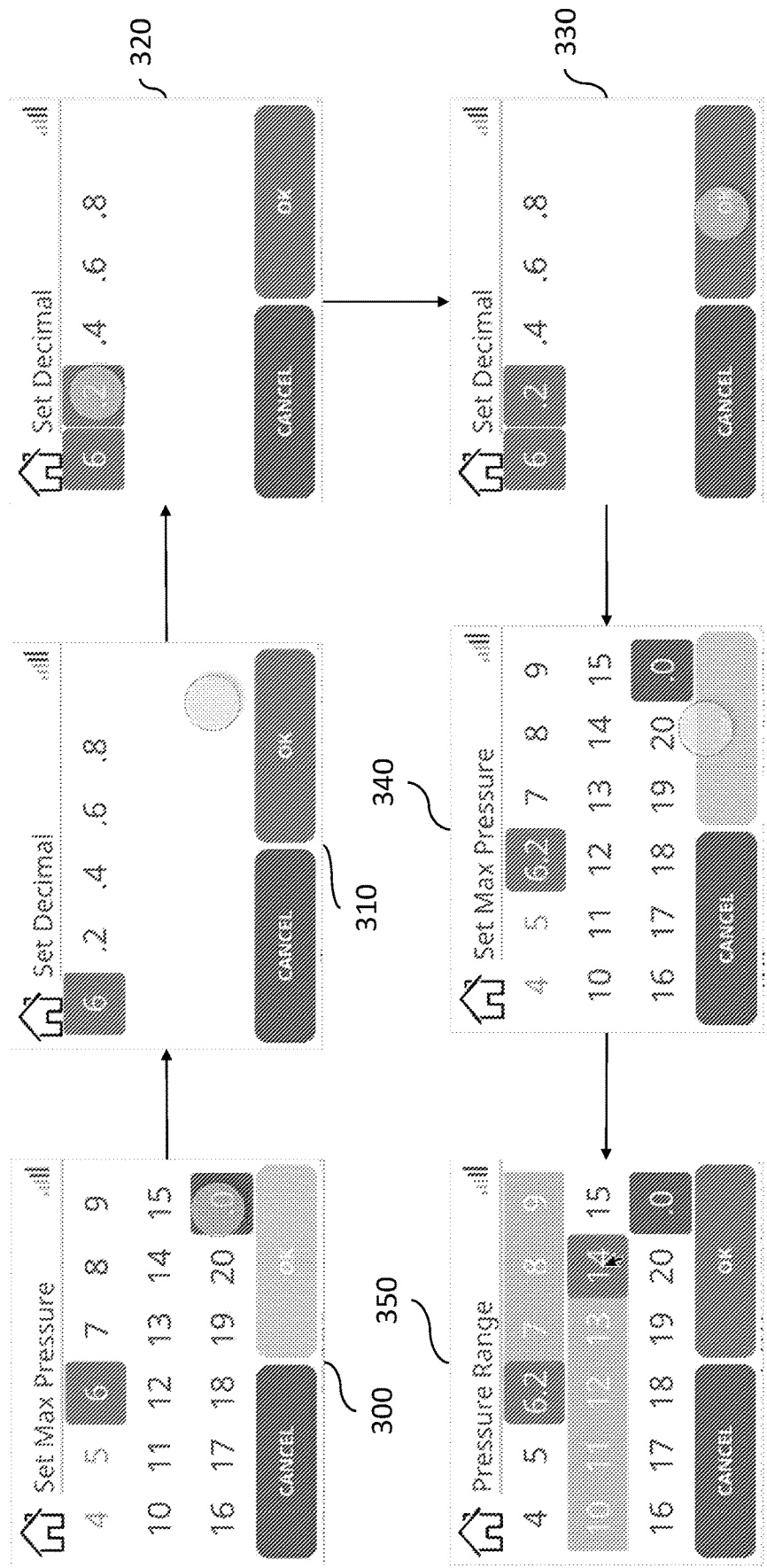
FIG. 3 shows a series of user interface screens of setting a pressure range with decimals on a ventilator of a PAP system according to certain examples.
Figure 4:
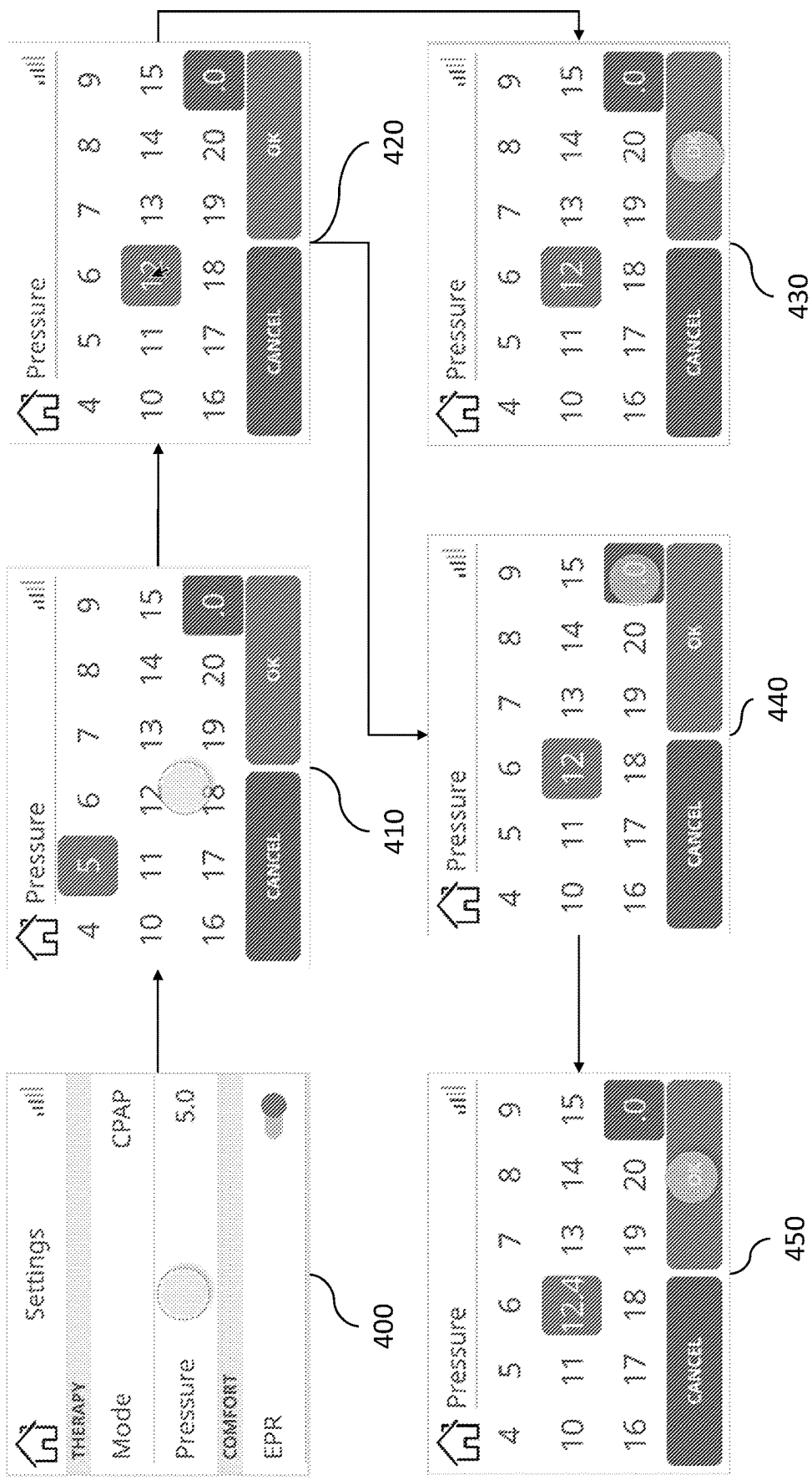
FIG. 4 shows a series of user interface screens of setting a pressure with or without decimals on a ventilator of a PAP system according to certain examples.
Figure 5:
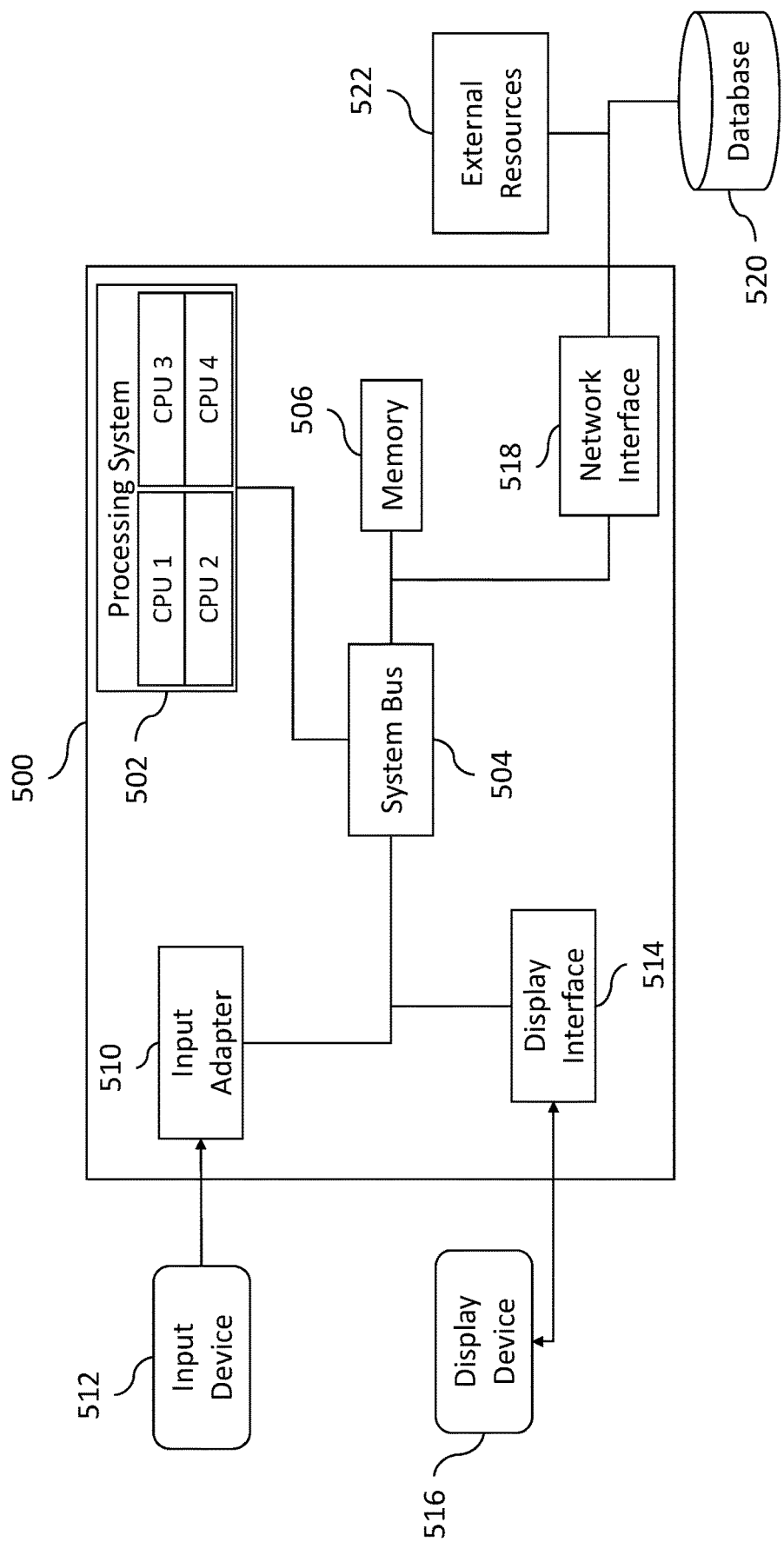
FIG. 5 shows an example computing device that may be used in some embodiments to implement features described herein.

In certain example embodiments, each or any of the user interface screens shown in FIG. 3-5 may be generated by a processor that is separate from processor 114 and/or display 160. Each or any of the user interface screens may be displayed on a display other than display 160 of the RPT device 108. Or the RPT device 108 may include a touch-screen that is separate from the housing that includes the flow generator or other components of the PAP system. For example, a mobile device or other computer system may be used to generate each or any of the display screens that are discussed in connection with FIGS. 3-5. Additionally, a display associated with such a mobile device or other computer system may be used to present such display screens. Accordingly, a user may interact with a mobile device or other computer system and such a system may communicate (e.g. via wired or wireless communication, such as network interface 518) with the RPT device (or components thereof) to thereby control the pressure based on the selected pressure aspects. In certain examples, display screens may be generated by a computer system separate from the RPT device 108 and communicated (e.g., as image data or the like) to the RPT device for display on display 160.

Patient interface 110 may include one or more of the following functional aspects: a seal-forming structure, a plenum chamber, a positioning and stabilizing structure, a vent, one form of a connection port for connection to conduit 152, and/or a forehead support. In certain examples, the functional aspect may be provided by one or more physical components. In some forms, one physical component may provide one or more functional aspects.

In certain examples, the seal-forming structure is arranged to surround an entrance to at least one airway of the patient so as to facilitate the supply of air at positive pressure to the at least one airway.

In certain examples, a patient interface that is unable to comfortably deliver a level of positive pressure to a patient's airways that is more than a threshold level may be unsuitable for respiratory pressure therapy. In certain examples, patient interface 110 may provide a supply of air at a positive pressure of at least 6 cmH2O, of at least 10 cmH2O, or of at least 20 cm H2O with respect to ambient air pressure.

In certain examples, a seal-forming structure of the patient interface provides a target seal-forming region, and may additionally provide a cushioning function. The target seal-forming region is a region on the seal-forming structure where sealing may occur. It will be appreciated that the region where sealing occurs may change within a given treatment session, from day to day, and from patient to patient, depending on a range of factors including, for example, where the patient interface was placed on the face, tension in the positioning and stabilizing structure and the shape of a patient's face.

In certain examples, the target seal-forming region is located on an outside surface of the seal-forming structure. In certain examples, the seal-forming structure is constructed from a biocompatible material (e.g., silicone rubber).

In certain examples, the seal-forming structure forms a seal on: 1) on a nose bridge region or on a nose-ridge region of the patient's face, 2) an upper lip region (e.g., the lip superior) of the patient's face, 3) a chin-region of the patient's face, and/or 4) a forehead region of the patient's face (e.g., where the plenum chamber may cover the eyes of the patient when the patient interface is worn by the patient). In certain examples, the seal-forming structure forms may comprise a pair of nasal puffs, or nasal pillows, each nasal puff or nasal pillow being constructed and arranged to form a seal with a respective naris of the nose of a patient In certain examples, the plenum chamber has a perimeter that is shaped to be complementary to the surface contour of the face of an average person in the region where a seal will be formed. When used by a patient, a marginal edge of the plenum chamber is positioned in close proximity to an adjacent surface of the face. Actual contact with the face may be provided by the seal-forming structure discussed herein. In certain examples, the seal-forming structure may extend about the entire perimeter of the plenum chamber. In certain examples, the plenum chamber and the seal-forming structure are formed from a single homogeneous piece of material.

In certain examples, the patient interface 110 may include positioning and stabilizing structures used to hold the patient interface in a sealing position on the face of the patient. In certain examples, the included positioning and stabilizing structure may include straps, ties, or other component that acts to secure the mask to the head of a patient.

In certain examples, the patient interface 110 may include a vent that is constructed to allow for the washout of exhaled gases (e.g., carbon dioxide) from the patient as a result of breathing. In certain examples, such a vent is configured to allow a continuous vent flow from an interior of the plenum chamber to ambient while the pressure within the plenum chamber is positive with respect to ambient. The vent may be configured such that the vent flow rate has a magnitude sufficient to reduce rebreathing of exhaled $CO_2$ by the patient while maintaining the therapeutic pressure in the plenum chamber while a patient interface is being used by the patient. In certain examples, the vent includes a plurality of holes, for example, about 20 to about 80 holes, or about 40 to about 60 holes, or about 45 to about 55 holes.

In certain examples, the patient interface 110 may include a connection port that allows for a structural coupling of the conduit 152 to patient interface to thereby deliver above atmospheric gas to the patient from the conduit 152.

In certain examples, the patient interface 110 includes a forehead support structural support that allows the patient interface to engage with the forehead of the patient.

In certain examples, conduit 152 is constructed to allow a flow of air between the flow generator 108 and the patient interface 110. In certain examples, conduit 152 includes one or more heating elements (e.g., a heated wire circuit) configured to heat the air in the air conduit 152. The heating element may be controlled by controller 156 of the flow generator 108.

Flow generator 108 includes controller 156, a communication interface 158, a pressure generator (not shown), and one or more displays (e.g., touch screen display 160). Flow generator 108 may include an outlet that is configured to couple to conduit 152. Flow generator may also include a blower that is configured to supply gas (e.g., breathable air) at pressure between about 2-40 cmH2O, or in the range of 4-20 cmH2O to patient interface 110 via an air delivery conduit 152. A flow sensor and/or a pressure sensor may be included at the outlet of the flow generator 108 and/or may be included with the patient interface 110 or conduit 152.

Controller 156 is used to control the functionality of the flow generator (e.g., adjust the speed of a blower in order to affect the pressure level that is being delivered) and may work in conjunction processor 114 to control the functionality of the flow generator 108. For example, software may be executed by the processor 114 that may then instruct the controller 156 to change the speed of a motor or the like. Communication interface 158 may be a communication or network interface such as that described in FIG. 5.

In one form of the present technology, a pressure generator for producing a flow, or a supply, of air at positive pressure is a controllable blower. For example, a blower may include a brushless DC motor with one or more impellers. The impellers may be located in a volute. The blower may be capable of delivering a supply of air, for example at a rate of up to about 120 liters/minute, at a positive pressure in a range from about 4 cmH2O to about 20 cmH2O, or in other forms up to about 30 cmH2O when delivering respiratory pressure therapy. The blower may be as described in any one of the following patents or patent applications the contents of which are incorporated herein by reference in their entirety: U.S. Pat. Nos. 7,866,944; 8,638,014; 8,636,479; and PCT Patent Application Publication No. WO 2013/020167. The pressure generator may be controllable via electric or electrical connections to the controller 156.

In certain examples, patient interface 110, conduit 152, flow generator 108, and/or other PAP component types (e.g., a humidifier, etc.) may include one or more identifying features that may be used to uniquely distinguish the type of component (e.g., a nasal mask versus a full mask mask) and/or a specific component being used by a patient (e.g., each component may have a unique identifier—e.g., a GUID) that is used to distinguish a particular component from other components (even if they are the same type of component). In certain examples, one identifying feature may be used to identify the type of PAP component and another may be used to specifically identify a particular PAP component. In certain examples, the identifying feature is implemented via a bar code, RFID (e.g., active or passive), a resister, or the like.

In certain examples, one or more of the PAP components may also include a memory device for storing data related to that PAP component (or other PAP components or usage data about a patient). The data may be for a specific patient (e.g., that is to use the component). In certain examples, the data may be accessed via wireless or wired data communications (e.g., via RFID). In certain examples, data from sensors for a given component may be written directly to a memory device of the PAP component carrying the sensor. For example, patient interface 110 may include a sensor for measuring pressure and a memory device (e.g., flash memory) disposed with the mask to storing pressure data recorded by the pressure sensor.

Figure 2:
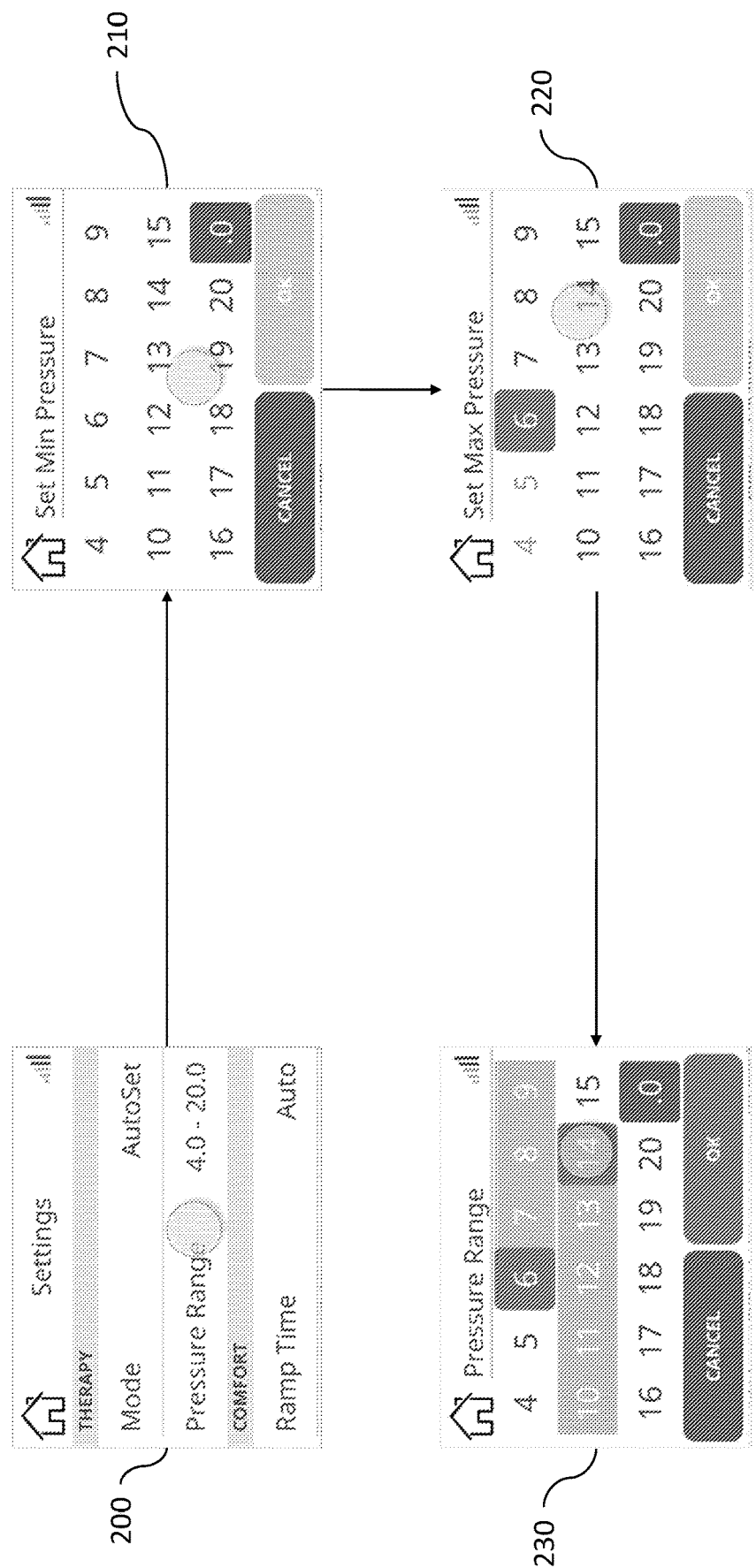
FIG. 2 shows a series of user interface screens of setting a pressure range on a ventilator of a PAP system according to certain examples.

FIG. 2: Set Pressure Range

FIG. 2 shows a series of user interface screens of setting a pressure range on a ventilator of a PAP system according to certain examples. The screens on FIG. 2 are shown in sequence, with user inputs being provided between the shown screens.

Screen 200 is an informational screen that shows the mode that the RPT device is currently in (AutoSet) and that the "ramp time" is set to auto. In certain examples, a user may click on the area associated with items and further menus may be displayed that allow a user to change the mode/ramp time. Providing a touch input in the area of the screen associated with the "Pressure Range" label will bring up a menu that allows for setting a pressure range (e.g., in terms of cmH2O). In certain example embodiments, the pressure range that is set may be used to control one or more properties of how the pressure is ramped up during treatment for the patient.

Screen 210 is loaded in response to a user indicating the pressure range area in screen 200. Screen 210 includes a list of numbers that correspond to the various pressure values that may be set by a user. A label at the top of the screen ("Set Min Pressure") indicates to the user that they are to set the minimum pressure for the pressure range setting.

In the lower left of screen 210 is a cancel button that will cancel this screen and return to the previous screen (e.g., screen 200). Similar functionality may be implemented for the other screens discussed herein.

In the lower right of screen 210 is an "OK" button. There may be two different states to the OK button. The first is shown in screen 210 in which the OK button is greyed out or changed in color. This may be used to indicate to the user that they still must perform an operation on this screen in order for a command to be accepted. If a user presses or otherwise selects the OK button while it is greyed out the system may not respond as the button is not yet active.

The second state of the OK button is when the conditions for a successful operation have been fulfilled. This is shown in screen 230 and other screens in FIGS. 3 and 4. In the second state the button is turned to a darker color. In the case of FIG. 2, this indicates that a valid range has been set and the user can set the range by selecting/pressing the OK button.

Another button shown in FIG. 2 is the decimal button of "0.0" in the lower right corner of screen 210. This button and the associated functionality will be discussed in connection with FIG. 3.

Screen 210 also include a circular element that is between the numbers 13 and 19. This is used to indicate where an input is currently located, but that the user has not yet indicated a selection. For example, the circle may indicate where a "mouse" cursor is located on the screen, but not where a user has "clicked" with the mouse. In a touch screen embodiment, the circle may indicate a touch location that is lighter than a touch input used for selection.

In any event, at screen 210 the user is prompted to select one of the numbers that is displayed as the lower end or minimum pressure for a set range.

Screen 220 shows the result of the selecting 6, this causes the screen to change the label at the top to now be "Set Max Pressure" and to grey out those values that are lower than 6 (e.g., to make them un-selectable). As shown in screen 220, "6" is highlighted (or otherwise visually changed) in response to be being selected.

Screen 230 shows the result of selection of 14 as the "max" of the range that is being set by the user provided inputs. This input also causes the label at the top of the screen to change to "Pressure Range." Further, as the range that is selected is now a valid range, the OK button is visually changed to indicate that the user can select the OK button. Selecting the OK button will then update a pressure range value that is used by the flow generator to supply air to a patient.

In certain examples, selecting the second number (which is valid) will then automatically set the range without having to select "OK." In other words, once "14" is selected the system may store 6-14 as the set range and return to the screen shown at 200 (e.g., the screens with the numbers may be automatically closed). In certain examples, once the range is selected as shown in 230, then the system may automatically accept the range (and return to screen 300) after a period of time (e.g., 2, 3, 5 seconds, or upon the expiration of any other timer).

In certain example embodiments, once a pressure range is accepted (e.g., when the user selects "OK"), then the pressure range is set for ramping between the low value (e.g., 6) to the high value (e.g., 14). Once set, the RPT device may then initiate a ramping of the pressure between the two selected values.

In certain example embodiments, one or more commands or instructions may be communicated (e.g., by using a wired or wireless transceiver, such as Bluetooth) to thereby control the pressure level in accordance with the numbers that have been selected via the touch screen.

It will appreciated that the number of inputs needed to set a pressure range may be decreased from other user interface screens. For example, the number in this example may be less than using a dial or a scroll wheel, etc.

FIG. 3: Set Pressure Range with Decimal

FIG. 3 shows a series of user interface screens for setting a pressure range with decimals on a ventilator of a PAP system according to certain examples. The screens shown in FIG. 3 may start from a similar screen show in 200 in FIG. 2. Indeed, screen 300, where a user has provided input to select "6" may be the same as screen 220. Unlike the series of screens shown in FIG. 2, here the user decides to set a factional amount for the minimum pressure of the pressure range.

Screen 300 shows the user about to select the "0.0" button (herein after referred to as the decimal button). Note that the decimal button may be displayed different than the other numbers in the screen. For example, it may be displayed with a white lettering with a black background. In certain examples, the decimal button may be un-selectable (like the "OK" button) if a number has not already been selected. In other words, the decimal button may become active in response to the user selecting one of the other numbers.

In any event, once the decimal button is selected, then a new user interface screen 310 is presented with options for selecting a decimal value. In certain example embodiments, user interface screen 310 (and associated screens) may replace, for example, screen 220. In certain examples, user interface screen 310 may be superimposed over screen 220 (e.g., both may be displayed at the same time). In any event, in screen 310, decimal values in increments of 0.2 are allowed, however other options are also possible (e.g., every 0.25 or every 0.1, etc.). In certain examples, fractions may be used instead of decimals (e.g., ¼ or ½).

When screen 310 is displayed the number that was previously (e.g., most recently) selected by the user in screen 300 ("6" in the example from FIG. 3) is shown in the upper left of the screen along with the series of decimal options.

In screen 320, decimal value 0.2 is shown as being selected by a user. The selection of one of the decimal values causes that value to be highlighted or otherwise indicated on the screen to the user.

In screen 330, once the user then accepts the decimal selection by selecting the OK button in the lower right of screen 300. This returns the display screen to setting the pressure range.

In screen 340, the display of the 6 that had been selected by the user in screen 300 has been updated to now include the decimal value selected via screens 310, 320, and 330. Accordingly, the minimum pressure value of the range is now set to "6.2."

In screen 350, the user then sets the max pressure for the range by selecting 14. It will be appreciated that the user may opt to also set a decimal value for the max range by selecting the decimal button and provided inputs in the same manner as described above.

FIG. 4: Set Pressure

In certain examples, the RPT device may include functionality for allowing a user to set a pressure via a user interface display that is provided on the RPT device. FIG. 4 shows a series of user interface screens of setting a pressure with or without decimals on an RPT device of a PAP system according to certain examples.

Screen 400 is a settings screen that includes values for a current mode (set to PAP in screen 400), and whether expiratory pressure relief is enabled (currently enabled in screen 400). The other option is the pressure setting, which is currently set to 5.0 cmH2O. Upon selecting the pressure label or its value, screen 410 is loaded and displayed to the user.

When screen 410 is loaded, the current pressure setting (5) may be highlighted as shown. A user may then select "cancel" to cancel the operation, OK to accept any changes, and/or select a new pressure value among those displayed (with or without a decimal modification).

Screen 420 shows the results of a user selecting "12." The previously highlighted 5 is unlighted as 12 is now selected.

Screen 430 is just before the user clicks the OK button to accept the set pressure change to 12.

As an alternative to screen 430, the user may also select the decimal button in screen 440. This will cause the decimal number screen to be shown to the user as is described in connection with FIG. 3.

Screen 450 shows the results of selecting "0.4" in the decimal number screen, and just before the user selects OK.

Selecting OK (in either screen 430 or 45) will cause the RPT device to set the pressure level to the indicated pressure level and return to screen 400 with the pressure level changed to a new value (if applicable).

Description of FIG. 5

FIG. 5 is a block diagram of an example computing device 500 (which may also be referred to, for example, as a "computing device," "computer system," or "computing system") herein. In certain examples, the computing device 500 includes one or more of the following: a processing system 502, which includes one or more hardware processors (e.g., central processing units or CPUs, GPUs, etc.); one or more memory devices 506; one or more network interface devices 518; one or more display interfaces 514; and one or more user input adapters 510. Elements of computing device 500 may communicate with one another via system bus 504. Additionally, in some examples, the computing device 500 is connected to or includes a display device 516, user input device 512, database 520, and/or external resources 522 (which may be another instance of computing device 500. As will be explained below, these elements (e.g., the processing system 502, memory devices 506, network interface devices 518, display interfaces 514, user input adapters 510, display device 516) are hardware devices (for example, electronic circuits or combinations of circuits) that are configured to perform various different functions for the computing device 500.

In some examples, each or any of the processors (e.g., CPUs 1, 2, 3, or 4) of the processing system 502 is or includes, for example, a single- or multi-core processor, a microprocessor (e.g., which may be referred to as a central processing unit or CPU), a digital signal processor (DSP), a microprocessor in association with a DSP core, an Application Specific Integrated Circuit (ASIC), a Field Programmable Gate Array (FPGA) circuit, and/or a system-on-a-chip (SOC) (e.g., an integrated circuit that includes a CPU and other hardware components such as memory, networking interfaces, and the like). In certain examples, each or any of the processors may use an instruction set architecture such as x86 or Advanced RISC Machine (ARM).

In some examples, each or any of the memory devices 506 is or includes a random access memory (RAM) (such as a Dynamic RAM (DRAM) or Static RAM (SRAM)), a flash memory (based on, e.g., NAND or NOR technology), a hard disk, a magneto-optical medium, an optical medium, cache memory, a register (e.g., that holds instructions), or other type of device that performs the volatile or non-volatile storage of data and/or instructions (e.g., software that is executed on or by processors of the processing system 502). Memory devices 506 are examples of non-transitory computer-readable storage media.

In some examples, each or any of the network interface devices 518 includes one or more circuits (such as a baseband processor and/or a wired or wireless transceiver), and implements layer one, layer two, and/or higher layers for one or more wired communications technologies (such as Ethernet (IEEE 802.3)) and/or wireless communications technologies (such as Bluetooth, WiFi (IEEE 802.11), GSM, CDMA2000, UMTS, LTE, LTE-Advanced (LTE-A), and/or other short-range, mid-range, and/or long-range wireless communications technologies). Transceivers may comprise circuitry for a transmitter and a receiver. The transmitter and receiver may share a common housing and may share some or all of the circuitry in the housing to perform transmission and reception. In some examples, the transmitter and receiver of a transceiver may not share any common circuitry and/or may be in the same or separate housings.

In some examples, each or any of the display interfaces 514 is or includes one or more circuits that receive data from the processors of the processing system 502, generate (e.g., via a discrete GPU, an integrated GPU, a CPU executing graphical processing, or the like) corresponding image data based on the received data, and/or output (e.g., a High-Definition Multimedia Interface (HDMI), a DisplayPort Interface, a Video Graphics Array (VGA) interface, a Digital Video Interface (DVI), or the like), the generated image data to the display device 616, which displays the image data. Alternatively, or additionally, in some examples, each or any of the display interfaces 514 is or includes, for example, a video card, video adapter, or graphics processing unit (GPU).

In some examples, each or any of the user input adapters 510 is or includes one or more circuits that receive and process user input data from one or more user input devices 512 that are included in, attached to, or otherwise in communication with the computing device 500, and that output data based on the received input data to the processors 502. Alternatively, or additionally, in some examples each or any of the user input adapters 510 is or includes, for example, a PS/2 interface, a USB interface, a touchscreen controller, or the like; and/or the user input adapters 510 facilitates input from user input devices 512, which may include, for example, a keyboard, mouse, trackpad, touchscreen, voice input, etc. In certain examples, user input adapter 510 may be configured to process data from other types of input sources that are not from a user. For example, user input adapter 510 (e.g., an input adapter) may process data from one or more sensors (e.g., flow, pressure, temperature, or other types of sensors).

In some examples, the display device 516 may be a Liquid Crystal Display (LCD) display, Light Emitting Diode (LED) display, or other type of display device. In examples where the display device 516 is a component of the computing device 500 (e.g., the computing device and the display device are included in a unified housing of, for example, a mobile or tablet device or within the housing a RPT device), the display device 516 may be a touchscreen display (e.g., using capacitive or resistive technology to sense the location of a provided input) or non-touchscreen display. In examples where the display device 516 is connected to the computing device 500 (e.g., is external to the computing device 500 and communicates with the computing device 500 via a wire and/or via wireless communication technology), the display device 516 is, for example, an external monitor, projector, television, display screen, etc.

In various examples, the computing device 500 includes one, or two, or three, four, or more of each or any of the above-mentioned elements (e.g., the processing system 502, CPUs 1, 2, 3, or 4, memory devices 506, network interface devices 518, display interfaces 514, and user input adapters 510). In some examples, the computing device 500 includes one or more of: a processing system 602 that includes hardware processors (e.g., CPUs 1, 2, 3, and/or 4); a memory or storage system that includes the memory devices; and a network interface system that includes the network interface devices 618.

The computing device 500 may be arranged, in various examples, in many different ways. As just one example, the computing device 500 may be arranged such that the processors include: a multi (or single)-core processor; a first network interface device (which implements, for example, WiFi, Bluetooth, NFC, etc.); a second network interface device that implements one or more cellular communication technologies (e.g., 3G, 4G LTE, CDMA, etc.); memory or storage devices (e.g., RAM, flash memory, or a hard disk). The processor, the first network interface device, the second network interface device, and the memory devices may be integrated as part of the same SOC (e.g., one integrated circuit chip). As another example, the computing device 500 may be arranged such that: the processors include two, three, four, five, or more multi-core processors; the network interface devices 518 include a first network interface device that implements Ethernet and a second network interface device that implements WiFi and/or Bluetooth; and the memory devices 506 may include RAM and storage in the form of flash memory or hard disk.

As previously noted, whenever it is described in this document that a software module or software process performs any action, the action is in actuality performed by underlying hardware elements according to the instructions that comprise the software module.

The hardware configurations shown in FIG. 5 and described above are provided as examples, and the subject matter described herein may be utilized in conjunction with a variety of different hardware architectures and elements. For example: in many of the Figures in this document, individual functional/action blocks are shown (e.g., the creation of each of the screens and the processes a user takes to interact with those screens); in various examples, the functions of those blocks may be implemented using (a) individual hardware circuits, (b) using an application specific integrated circuit (ASIC) specifically configured to perform the described functions/actions, (c) using one or more digital signal processors (DSPs) specifically configured to perform the described functions/actions, (d) using the hardware configuration described above with reference to FIG. 5, (e) via other hardware arrangements, architectures, and configurations, and/or via combinations of the technology described in (a) through (e).

In certain examples, the techniques herein provide for an improved user interface that allows users to more efficiently and/or quickly set pressure and other parameters that are used by an RPT device Whenever it is described in this document that a given item is present in "some embodiments," "various embodiments," "certain embodiments," "certain example embodiments, "some example embodiments," "an exemplary embodiment," "certain examples," "some examples," or whenever any other similar language is used, it should be understood that the given item is present in at least one embodiment or example, though is not necessarily present in all embodiments or examples. Consistent with the foregoing, whenever it is described in this document that an action "may," "can," or "could" be performed, that a feature, element, or component "may," "can," or "could" be included in or is applicable to a given context, that a given item "may," "can," or "could" possess a given attribute, or whenever any similar phrase involving the term "may," "can," or "could" is used, it should be understood that the given action, feature, element, component, attribute, etc. is present in at least one example or embodiment, though is not necessarily present in all embodiments or examples. Terms and phrases used in this document, and variations thereof, unless otherwise expressly stated, should be construed as open-ended rather than limiting. As examples of the foregoing: "and/or" includes any and all combinations of one or more of the associated listed items (e.g., a and/or b means a, b, or a and b); the singular forms "a", "an" and "the" should be read as meaning "at least one," "one or more," or the like; the term "example" is used to provide examples of the subject under discussion, not an exhaustive or limiting list thereof; the terms "comprise" and "include" (and other conjugations and other variations thereof) specify the presence of the associated listed items but do not preclude the presence or addition of one or more other items; and if an item is described as "optional," such description should not be understood to indicate that other items are also not optional.

As used herein, the term "non-transitory computer-readable storage medium" includes a register, a cache memory, a ROM, a semiconductor memory device (such as a D-RAM, S-RAM, or other RAM), a magnetic medium such as a flash memory, a hard disk, a magneto-optical medium, an optical medium such as a CD-ROM, a DVD, or Blu-Ray Disc, or other type of device for non-transitory electronic data storage. The term "non-transitory computer-readable storage medium" does not include a transitory, propagating electromagnetic signal.

While certain examples are described in connection with PAP systems, it will be appreciated that the techniques herein may be applicable to other types of home medical equipment.

Although process steps, algorithms or the like, may be described or claimed in a particular sequential order, such processes may be configured to work in different orders. In other words, any sequence or order of steps that may be explicitly described or claimed in this document does not necessarily indicate a requirement that the steps be performed in that order; rather, the steps of processes described herein may be performed in any order possible. Further, some steps may be performed simultaneously (or in parallel) despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary, and does not imply that the illustrated process is preferred.

Although various embodiments and examples have been shown and described in detail, the claims are not limited to any particular embodiment or example. None of the above description should be read as implying that any particular element, step, range, or function is essential. All structural and functional equivalents to the elements of the above-described embodiments and examples that are known to those of ordinary skill in the art are expressly incorporated herein by reference and are intended to be encompassed. Moreover, it is not necessary for a device or method to address each and every problem sought to be solved by the present invention, for it to be encompassed by the invention. No embodiment, example, feature, element, component, or step in this document is intended to be dedicated to the public.

The invention claimed is:

1. A non-transitory computer readable storage medium configured to store computer executable instructions for use with a processing system that includes at least one hardware processor, the stored computer executable instructions comprising instructions that cause the processing system to perform operations comprising:
    outputting, to a display for display thereon, a first pressure control user interface display screen that includes a plurality of numbers that indicate pressure values that correspond to positive pressure levels that a flow generator is configured to provide as part of positive airway pressure provided to a patient interface device;
    processing a first selection input that is provided to select a first value out of the plurality of numbers that are displayed as part of the first pressure control user interface display screen;
    outputting, to the display for display thereon, a second pressure control user interface display screen that is based on user input provided in connection with the first pressure control user interface display screen, wherein the second pressure control user interface display screen includes a plurality of incremental values that are different from the plurality of numbers and allowed to be selected;
    processing a second selection input that is provided to select one of the plurality of incremental values that are displayed as part of the second pressure control user interface display screen;
    automatically updating, based on which one of the plurality of incremental values was selected, the first value to be an adjusted value that is selected and part of the displayed first pressure control user interface display screen, the adjusted value based on a combination of the first value and the selected one of the plurality of incremental values; and
    instructing the flow generator to control a pressure level at which the positive airway pressure is provided to the patient interface device in accordance with the adjusted value.

2. The non-transitory computer readable storage medium of claim 1, wherein each of the plurality of numbers is an integer.

3. The non-transitory computer readable storage medium of claim 2, wherein each of the plurality of incremental values that are displayed are fractional values.

4. The non-transitory computer readable storage medium of claim 3, wherein each of the plurality of incremental values that are displayed are displayed as a decimal value that is less than one.

5. The non-transitory computer readable storage medium of claim 1, wherein the first pressure control user interface display screen and the second pressure control user interface are displayed at different times on the display.

6. The non-transitory computer readable storage medium of claim 1, wherein the operations further comprise:
processing a third selection input that is provided to select a second value out of the plurality of numbers that are displayed as part of the first pressure control user interface display screen,
wherein control of the pressure level is further based on the selected second value.

7. The non-transitory computer readable storage medium of claim 6, wherein the operations further comprise:
processing the user input that is provided while the first pressure control user interface display screen is displayed; and
based on processing the further input, transitioning to outputting the second pressure control user interface to the display for display thereon,
wherein based on processing of the second selection input to select one of the plurality of incremental values, transitioning back to outputting the first pressure control user interface to the display for display thereon.

8. The non-transitory computer readable storage medium of claim 6, wherein the pressure level is controlled during a treatment period to be within a range that is based on the adjusted value and the selected second value.

9. The non-transitory computer readable storage medium of claim 6, wherein the operations further comprise:
changing how those ones of the plurality of numbers that are between the first selected value and the second selected value are displayed.

10. The non-transitory computer readable storage medium of claim 1, wherein the operations further comprise:
based on selection of the first selected value, adjust how those ones of the plurality of numbers that are less than the selected value are displayed to indicate that those ones of the plurality of numbers are not selectable.

11. The non-transitory computer readable storage medium of claim 1, wherein the second pressure control user interface display screen is generated to include the first value out of the plurality of numbers that have been selected with the first selection input.

12. A system comprising:
a processing system comprising instructions that, when executed by at least one hardware processor included with the processing system, cause the at least one hardware processor to perform operations comprising:
outputting, to a display for display thereon, a first pressure control user interface display screen that includes a plurality of numbers that indicate pressure values that correspond to positive pressure levels that a flow generator is configured to provide as part of positive airway pressure provided to a patient interface device;
processing a first selection input that is provided to select a first value out of the plurality of numbers that are displayed as part of the first pressure control user interface display screen;
outputting, to the display for display thereon, a second pressure control user interface display screen that is based on user input provided in connection with the first pressure control user interface display screen, wherein the second pressure control user interface display screen includes a plurality of incremental values that are different from the plurality of numbers and allowed to be selected;
processing a second selection input that is provided to select one of the plurality of incremental values that are displayed as part of the second pressure control user interface display screen;
automatically replacing, based on which one of the plurality of incremental values was selected, the first value with an adjusted value that is selected, displayed, and part of the displayed first pressure control user interface display screen, the adjusted value based on a combination of the first value and the selected one of the plurality of incremental values; and
instructing the flow generator to control a pressure level at which the positive airway pressure is provided to the patient interface device in accordance with the adjusted value.

13. The system of claim 12, further comprising:
the display that is a touch screen display configured to accept touch inputs, which include the first selection input and the second selection input, in conjunction with displaying of the first pressure control user interface display screen and the second pressure control user interface display screen; and
a housing that includes the flow generator and the display.

14. The system of claim 13, wherein the processing system is coupled to a first transceiver, wherein the housing includes a second transceiver, wherein the first and second transceivers are configured to communicate to carry out the instructing the flow generator to control the pressure level at which the positive airway pressure is provided to the patient interface device in accordance with the adjusted value.

15. The system of claim 12, wherein the operations further comprise:
processing a third selection input that is provided to select a second value out of the plurality of numbers that are displayed as part of the first pressure control user interface display screen,
wherein control of the pressure level is further based on the selected second value.

16. The system of claim 15, wherein the operations further comprise:
processing a further input that is provided while the first pressure control user interface display screen is displayed; and
based on processing the further input, transitioning to outputting the second pressure control user interface to the display for display thereon,
wherein based on processing of the second selection input to select one of the plurality of incremental values, transitioning back to outputting the first pressure control user interface to the display for display thereon.

17. The system of claim 15, wherein the pressure level is controlled during a treatment period to be within a range that is based on the adjusted value and the selected second value.

18. The system of claim 15, wherein the operations further comprise:
changing how those ones of the plurality of numbers that are between the first selected value and the second selected value are displayed.

19. The system of claim 12, wherein the processing system is included in a mobile device that includes the display and is configured to wirelessly communicate with the flow generator to control, at least in part, the pressure level at which the positive airway pressure is provided.

20. The system of claim 12, wherein the second pressure control user interface display screen is generated to include the first value out of the plurality of numbers that have been selected with the first selection input.

\* \* \* \* \*